United States Patent
Knox et al.

(10) Patent No.: US 10,838,233 B2
(45) Date of Patent: Nov. 17, 2020

(54) REFRACTIVE CORRECTOR INCORPORATING A CONTINUOUS CENTRAL PHASE ZONE AND PERIPHERAL PHASE DISCONTINUITIES

(71) Applicants: Wayne H. Knox, Pittsford, NY (US); Gustavo A. Gandara-Montano, Rochester, NY (US); Leonard Zheleznyak, Pittsford, NY (US)

(72) Inventors: Wayne H. Knox, Pittsford, NY (US); Gustavo A. Gandara-Montano, Rochester, NY (US); Leonard Zheleznyak, Pittsford, NY (US)

(73) Assignee: University of Rochester, Rochester, NY (US)

( * ) Notice: Subject to any disclaimer, the term of this patent is extended or adjusted under 35 U.S.C. 154(b) by 76 days.

(21) Appl. No.: 16/062,241

(22) PCT Filed: Dec. 14, 2016

(86) PCT No.: PCT/US2016/066625
§ 371 (c)(1),
(2) Date: Jun. 14, 2018

(87) PCT Pub. No.: WO2017/106321
PCT Pub. Date: Jun. 22, 2017

(65) Prior Publication Data
US 2018/0373060 A1 Dec. 27, 2018

Related U.S. Application Data

(60) Provisional application No. 62/267,577, filed on Dec. 15, 2015.

(51) Int. Cl.
G02C 7/04 (2006.01)
A61F 2/16 (2006.01)
(Continued)

(52) U.S. Cl.
CPC ............... *G02C 7/044* (2013.01); *A61F 2/14* (2013.01); *A61F 2/1656* (2013.01);
(Continued)

(58) Field of Classification Search
CPC ....... G02C 7/044; G02C 2202/20; A61F 2/14; A61F 2/1656; A61F 9/00827;
(Continued)

(56) References Cited

U.S. PATENT DOCUMENTS 7,073,906 B1† 7/2006 Portney
8,292,952 B2† 10/2012 Bille
(Continued)

FOREIGN PATENT DOCUMENTS

DE 19926512 A1 * 12/2000 ........... A61F 2/1654

*Primary Examiner* — Collin X Beatty
(74) *Attorney, Agent, or Firm* — Andrew J. Anderson, Esq.; Harter Secrest & Emery LLP

(57) ABSTRACT

Described refractive correctors, include, but are not limited to, intraocular lenses (IOLs), contact lenses, corneal inlays, and other optical components or devices, incorporating a continuous central phase zone and peripheral phase discontinuities. Further embodiments are directed to a method for using a laser to modify the refractive properties of refractive correctors to form such continuous central phase zone and peripheral phase discontinuities, and other applications. The refractive corrector and methods adapt a Fresnel lens structure to include continuous phase retarding regions having a wavefront height of greater than one design wavelength in a central zone of a refractive corrector to improve human vision applications, while maintaining benefits of phase wrapping in the peripheral region.

23 Claims, 7 Drawing Sheets

(51) Int. Cl.
*A61F 9/008* (2006.01)
*A61F 2/14* (2006.01)
*A61F 9/007* (2006.01)

(52) U.S. Cl.
CPC .......... *A61F 9/00827* (2013.01); *A61F 9/007* (2013.01); *A61F 2009/0087* (2013.01); *A61F 2009/00842* (2013.01); *A61F 2009/00872* (2013.01); *A61F 2250/0053* (2013.01); *G02C 2202/20* (2013.01)

(58) Field of Classification Search
CPC ............ A61F 9/007; A61F 2009/00842; A61F 2009/0087; A61F 2009/00872; A61F 2250/0053
USPC .................................................... 351/159.41
See application file for complete search history.

(56) References Cited

U.S. PATENT DOCUMENTS

| | | | |
|---|---|---|---|
| 8,480,228 B2 † | 7/2013 | Weeber | |
| 8,512,320 B1 * | 8/2013 | Knox | A61F 9/008 606/5 |
| 8,568,627 B2 † | 10/2013 | Bille | |
| 8,920,690 B2 † | 12/2014 | Bille | |
| 9,023,257 B2 † | 5/2015 | Sahler | |
| 9,925,621 B2 † | 3/2018 | Sahler | |
| 2002/0100990 A1 * | 8/2002 | Platt | A61F 2/1627 264/1.38 |
| 2010/0082017 A1 † | 4/2010 | Zickler | |
| 2010/0110382 A1 * | 5/2010 | Legerton | G02C 7/04 351/247 |
| 2010/0228345 A1 * | 9/2010 | Bille | A61B 5/0086 623/6.23 |
| 2014/0378955 A1 * | 12/2014 | Gray | A61F 9/00827 606/5 |
| 2015/0081016 A1 * | 3/2015 | De Sio | G02C 7/04 623/6.22 |

\* cited by examiner
† cited by third party

REFRACTIVE CORRECTOR INCORPORATING A CONTINUOUS CENTRAL PHASE ZONE AND PERIPHERAL PHASE DISCONTINUITIES

BACKGROUND

The disclosure is directed towards refractive correctors including, but are not limited to, intraocular lenses (IOLs), contact lenses, corneal inlays, and other optical components or devices, incorporating a continuous central phase zone and peripheral phase discontinuities. Further embodiments are directed to a method for using a laser to modify the refractive properties of refractive correctors to form such continuous central phase zone and peripheral phase discontinuities, and other applications.

In general, there are two types of intraocular lenses, referred to as pseudo-phakic IOLs and phakic IOLs. The former type replaces the eye's natural, crystalline lens, usually to replace a cataractous lens that has been removed. The latter type is used to supplement an existing lens and functions as a permanent corrective lens, which is implanted in the anterior or posterior chamber to correct refractive errors of the eye. Common techniques for forming intraocular lenses include molding, or machining such as by lathing and milling, to form a lens with desired shape and power. The power of the lens (i.e., point focus on the retina from light originating at infinity) to be implanted is determined based on pre-operative measurements of ocular length and corneal curvature of each patient. The pre-operative measurements are conducted with the hope that the patient will need little, if any, vision correction following the surgery. Unfortunately, due to errors in measurement, variable lens positioning, or wound healing, most patients undergoing surgery will not enjoy optimal vision without some form of vision correction following the surgery. Since the power of a typical (non-accommodating) IOL is fixed and cannot be adjusted post-implantation (in-situ), most patients must use corrective lenses such as eye glasses or contact lenses following cataract surgery to optimize their vision.

One potential alternative to post-operative, corrective lenses is a light-adjustable intraocular lens whose refractive properties can be modified following insertion of the lens into a human eye. One such lens, e.g., is reported in U.S. Pat. No. 6,450,642, wherein the light-adjustable lens is said to comprise (i) a first polymer matrix and (ii) a refraction modulating composition (RMC) that is capable of stimulus-induced polymerization. As stated, when a portion of the described lens is exposed to light of sufficient intensity, the RMC forms a second polymer matrix. The process results in a light adjusted, power-modified lens, wherein the power of the lens is changed by a shape change caused by migration of the RMC and subsequent polymerization(s).

U.S. Pat. No. 7,105,110 describes a method and instrument to irradiate a light adjustable lens as described in the Calhoun Patent with an appropriate amount of radiation in an appropriate pattern. The method is said to include aligning a source of the modifying radiation so as to impinge the radiation onto the lens in a pattern, and controlling the quantity of the impinging radiation. The quantity of the impinging radiation is controlled by controlling the intensity and duration of the irradiation.

As opposed to modifying the shape of a lens to change its power, U.S. Publication No. 2008/0001320 describes methods for modifying the refractive index of optical polymeric materials using very short pulses from a visible or near-IR laser having a pulse energy from 0.5 nJ to 1000 nJ, where the intensity of light is sufficient to change the refractive index of the material within the focal volume, whereas portions just outside the focal volume are minimally affected by the laser light. Irradiation within the focal volume results in refractive optical structures characterized by a positive change in refractive index of 0.005 or more relative to the index of refraction of the bulk (non-irradiated) polymeric material. Under certain irradiation conditions and in certain optical materials, a change in refractive index of 0.06 was measured. The irradiated regions of the optical material can take the form of two- or three-dimensional, area or volume filled refractive structures. The refractive structures are formed by scanning the laser over a select region of the polymeric material resulting in refractive optical structures that can provide spherical, aspherical, toroidal, or cylindrical correction to a lens. In fact, any optical structure can be formed to yield positive or negative power corrections to the lens. Moreover, the optical structures can be stacked vertically or written in separate planes in the polymeric material to act as a single lens element. U.S. Pat. No. 7,789,910 further describes using Raman spectroscopy as an investigative approach to determine what, if any, structural, chemical or molecular change is occurring within the focal volume of the optical polymeric materials that might explain the observed change in the index of refraction.

U.S. Publication No. 2009/0287306 describes a similar process to provide dioptric power changes in optical polymeric materials that contain a photosensitizer. The photosensitizer is present in the polymeric material to enhance the photoefficiency of the two-photon process used to form the refractive structures. In some instances, the rate at which the laser light is scanned across the polymeric material can be increased 100-fold with the inclusion of a photosensitizer and still provide a similar change in the refractive index of the material.

U.S. Publication No. 2009/0157178 is said to describe a polymeric intraocular lens material that can provide a photoinduced, chemical change in the material resulting in a change in focal length (power) or the aspheric character of the lens by modifying the index of refraction of the material with laser light. The photoinduced chemistry in the material is said to occur by exposure of the material to laser light over a broad spectral range of 200 nm to 1500 nm.

U.S. Publication No. 2010/0228345 is said to describe a lens such as an intraocular lens in which the refractive index within a laser focus (loci) are modified to a depth of 5 μm to 50 μm. The method is said to provide dioptric power changes to the lens by a change in refractive index ($\Delta n$) of the lens material at different locus positions, e.g., between a lowest value of $\Delta n=0.001$ to a highest value of $\Delta n=0.01$. U.S. Publication No. 2010/0228345 further proposes to employ a modulo $2\pi$ phase wrapping technique across the lens surface, whereby only individual phase shifts of 0-$2\pi$ are written across the lens. The described irradiation method uses bursts of femtosecond (fs) laser pulses to change the refractive index of the irradiated material through a multiphoton absorption mechanism.

U.S. Publication No. 2012/0310340 describes a method for providing changes in refractive power of an optical device made of an optical, polymeric material by forming at least one laser-modified, gradient index (GRIN) layer disposed between an anterior surface and a posterior surface of the device by scanning with light pulses from a visible or near-IR laser along regions of the optical, polymeric material. The at least one laser-modified GRIN layer comprises a plurality of adjacent refractive segments, and is further characterized by a variation in index of refraction of at least one of: (i) a portion of the adjacent refractive segments transverse to the direction scanned; and (ii) a portion of refractive segments along the direction scanned. U.S. Publication 2012/0310223 discloses a method of modifying the refractive index in ocular tissues wherein a laser-modified gradient index (GRIN) layer is formed directly in at least one of the corneal stroma and the crystalline lens. U.S. 2012/0310340 and 2010/0310223 each further discloses that the design of the gradient index structures can be modified to provide a phase shift that is modulo-$2\pi$ to reduce the total device writing times.

Writing a phase shift profile in modulo-$2n$ form is done by subtracting a constant phase shift of $2\pi$ from the total design phase shift in the regions where the total design phase shift is between $2\pi$ and $4\pi$, subtracting a constant $4\pi$ phase shift from the total design phase shift in the regions where the total design phase shift is in the range $4\pi$ to $6\pi$, etc., in a "Fresnel" lens type pattern so that only resulting net phase shifts of $0$-$2\pi$ need to be written. Augustin-Jean Fresnel is widely credited with inventing the Fresnel lens for lighthouse applications. A Fresnel lens is much thinner and lighter than a continuous profile glass lens of the same diameter and focal length, since much of the bulk of the glass is removed by Fresnel's design. The concept of the Fresnel lens is shown in FIG. 1b, for a corresponding conventional continuous refractive lens shown in FIG. 1a (reproduced from "The Phase Fresnel Lens," K. Miyamoto, JOSA 51, 1, p. 17 (1959)). A continuous phase front is sampled into increments of $2\pi$ phase shift based on a design wavelength $\lambda$ and a discontinuous phase structure is produced. In this type of Fresnel lens design, the sampled phase regions occupy the entire lens surface and the phase discontinuities do not exceed $2\pi$ anywhere. In the conventional kind of Fresnel lens as described by Miyamoto, it can be advantageous in the fabrication procedure to only have to create phase shifts up to $2\pi$, however such a lens fundamentally has a large chromatic aberration which can be undesirable if not being used to correct for other chromatic aberrations in a system.

In order to obtain multi-focality which can be helpful in cases of presbyopia, it has been proposed and demonstrated that refracting base lenses can be augmented by placing diffractive steps across the lens diameter, or selectively either into a central region of the lens (see, e.g., "History and development of the apodized diffractive intraocular lens," J. A. Davison, M. J. Simpson, J Cataract and Refractive Surgery, VOL 32, p. 849, (2006)), or into an outer peripheral region of the lens (see, e.g., US 2010/0131060). When added selectively to the central region, e.g., in high light levels the contraction of the pupil effectively apodizes the lens, allowing light to pass through only the central diffractive step zone region. To obtain multi-focality, the phase shift profile is not in modulo-$2n$ form; rather the diffractive steps in such lenses have phase shifts of less than $2\pi$ so that collimated light is out of phase between such steps.

There is an ongoing need for new and improved techniques and materials, and refractive corrector vision components resulting therefrom, for improving human vision. Such components may include IOLs for use following cataract surgery, or may be in the form of corneal inlays or other implantable vision correction devices. There are also advantages and benefits that would result from such techniques and components allowing in-situ modification of refractive properties (e.g., refractive index, dioptric power) of such components, as well as direct modification of ocular tissue to provide corrected vision.

SUMMARY

According to aspects illustrated herein, there is provided a refractive corrector comprising:

(a) a central zone having a continuous wavefront cross-section phase profile, having a wavefront maximum height of greater than 1 design wavelength $\lambda$ in the area of the central zone; and (b) a peripheral region comprising multiple segments and having a discontinuous wavefront cross-section phase profile having phase shifts between segments that are equal to the design wavelength or multiples of the design wavelength, and wherein the phase shifts in the peripheral region are less than or equal to the wavefront maximum height in the central zone.

According to other aspects, a method of forming a refractive corrector is described comprising:

providing an optical, polymeric lens material having an anterior surface and posterior surface and an optical axis intersecting the surfaces; and forming at least one laser-modified layer disposed between the anterior surface and the posterior surface with light pulses from a laser by scanning the light pulses along regions of the optical, polymeric material to cause changes in the refractive index of the polymeric lens material;

wherein the optical, polymeric lens material comprises (a) a central zone having a continuous wavefront cross-section phase profile, having a wavefront maximum height of greater than 1 design wavelength $\lambda$ in the area of the central zone, and (b) a peripheral region comprising multiple segments and having a discontinuous wavefront cross-section phase profile having phase shifts between segments that are equal to the design wavelength or multiples of the design wavelength, wherein the phase shifts in the peripheral region are less than or equal to the wavefront maximum height in the central zone;

and wherein the at least one laser-modified layer forms at least part of at least one of the central zone or the peripheral region.

According to other aspects, a method for modifying a refractive property of ocular tissue in an eye is described, comprising:

forming at least one optically-modified layer in at least one of the corneal stroma and the crystalline lens ocular tissue in an eye by scanning light pulses from a laser focused in the corneal stroma or crystalline lens ocular tissue along regions of the corneal stroma or crystalline lens ocular tissue to cause changes in the refractive index within the ocular tissue to form a modified corneal stroma or crystalline lens;

wherein the modified corneal stroma or crystalline lens comprises (a) a central zone having a continuous wavefront cross-section phase profile, having a wavefront maximum height of greater than 1 design wavelength $\lambda$ in the area of the central zone, and (b) a peripheral region comprising multiple segments and having a discontinuous wavefront cross-section phase profile having phase shifts between segments that are equal to the design wavelength or multiples of the design wavelength, wherein the phase shifts in the peripheral region are less than or equal to the wavefront maximum height in the central zone;

and wherein the at least one optically-modified layer forms at least part of at least one of the central zone or the peripheral region.

In various embodiments, the central zone has a phase height greater than the phase shifts in the peripheral region.

In various embodiments, the peripheral region has a Fresnel structure having a phase shift between segments equal to the design wavelength.

In various embodiments, the peripheral region may more specifically circumscribe the central zone.

In various embodiments, an outer perimeter of the central zone and an outer perimeter of the peripheral region may be circular.

In various embodiments, an optical surface of the central zone more specifically may be parabolic, may be hyperbolic, may be a freeform surface, or may be aspheric.

In various embodiments, the central zone may have an outer diameter of at least 10, at least 20, at least 25, or at least 30% of the outer diameter of the peripheral region, e.g., from 10% to 90%, from 20% to 80%, from 25% to 75%, or from 30% to 70% of the outer diameter of the peripheral region.

In various embodiments the refractive corrector may be a contact lens or an intra-ocular lens.

In various embodiments, the peripheral region may have a phase profile sampled into $2\pi$ phase discontinuities.

In various embodiments, at least one of the central zone or peripheral region may comprise materials of varying refractive index contributing to the wavefront cross-section phase profile.

In various embodiments, the refractive corrector may be mono-focal for the design wavelength.

In various embodiments, the design wavelength may be a wavelength between 400 nm and 700 nm.

In various embodiments the design wavelength may be 555 nm.

The refractive corrector and method disclosed herein advantageously apply the basic Fresnel lens idea to a new area of human vision correction, by adapting the Fresnel lens structure to include continuous phase retarding regions having a wavefront height of greater than 1 design wavelength in a central zone of a refractive corrector. Based on our evaluation of the visual effects resulting from the use of this design, we have found that it is advantageous for human vision applications to include such a continuous phase central zone into a discontinuous phase Fresnel-type refractive corrector structure.

DETAILED DESCRIPTION

Figure 1A:
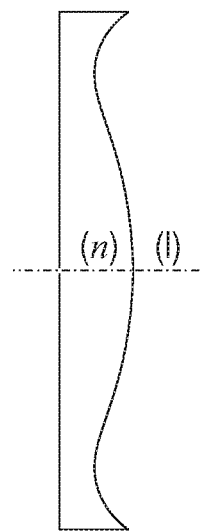
FIGS. 1a and 1b (Prior Art) provide an illustration of a modulo-$2\pi$ phase wrapped Fresnel lens (FIG. 1b), for a corresponding conventional continuous refractive lens (FIG. 1a).
Figure 1B:
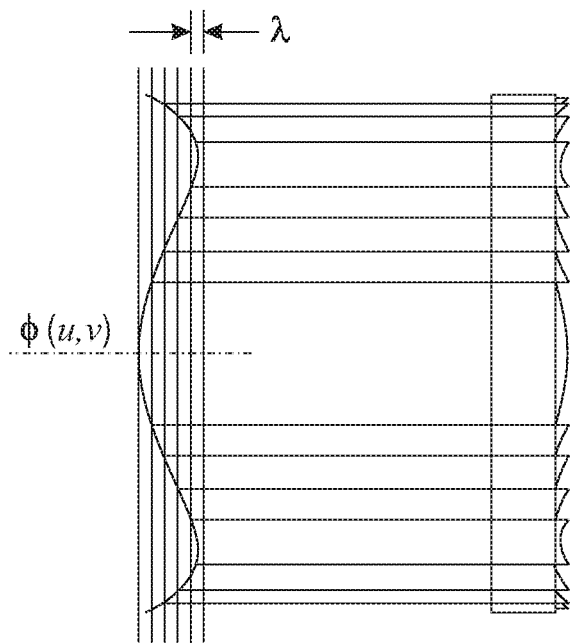

Custom refractive correctors may be written into contact lenses, intra-ocular lenses or directly into the cornea. The time required for such a writing procedure depends on how much total phase accumulation is required to create the desired refractive correction. Any medical procedure in humans will have time limits imposed by various factors, including safety, practicality, etc. In such a case, the use of Fresnel-type phase wrapped designs for the refractive corrector can be advantageous, since it enables writing the equivalent of a desired conventional continuous refractive phase shift pattern having a total maximum phase shift of greater than $2\pi$ in a refractive corrector with only a maximum net phase shift of $2\pi$. Conventional continuous refracting lenses, however, have certain advantages over discontinuous Fresnel-type correctors. For instance, they have significantly lower chromatic aberration than Fresnel-type correctors, since they are simply limited by material dispersion. Furthermore they can in principle exhibit higher optical quality including lower scattering losses compared to Fresnel-type structures if the Fresnel-type structures do not have perfect phase discontinuities.

In accordance with various disclosed embodiments, designs and methods for implementing mixed Fresnel-type refractive correctors are described that incorporate a central zone of continuous phase shift, and a peripheral Fresnel-type discontinuous phase shifting region. The central zone of continuous phase shift more particularly has a continuous wavefront cross-section phase profile, having a wavefront maximum height of greater than 1 design wavelength $\lambda$ in the area of the central zone. Thus, the central zone differs from the central zone in a conventional modulo $2\pi$ phase wrapped refractive corrector. The peripheral discontinuous phase shifting region, on the other hand, more particularly comprises multiple segments and having a discontinuous wavefront cross-section phase profile having phase shifts between segments that are equal to the design wavelength (consistent with a conventional modulo $2\pi$ phase rapped region), or multiples of the design wavelength. Further, the phase shifts in the peripheral region are less than or equal to the wavefront maximum height in the central zone. When the central zone has a phase height greater than the phase shifts in the peripheral region, the combined advantages of providing a significant central continuous zone while still enabling decreased write time for the combined continuous and discontinuous sections may be achieved. When the peripheral region has phase shifts between segments that are equal to the design wavelength (i.e., where the peripheral region has a phase profile sampled into a phase discontinuities), the further advantage of minimizing write time in the peripheral region may be achieved.

In various embodiments, the peripheral region may more specifically circumscribe the central zone. In further embodiments, an outer perimeter of the central zone and an outer perimeter of the peripheral region may be circular. In further non-limiting embodiments, an optical surface of the central zone further more specifically may be parabolic, may be hyperbolic, may be a freeform surface, or may be aspheric. For refractive correctors intended for visual correction, the design wavelength may be, e.g., in the visible range of between 400 and 700 nm, and in particular embodiments within the range of from 500-600 nm, or even more specifically within the range of from 550-560. More particularly, the design wavelength for the refractive corrector may be, e.g., 555 nm.

As the phase shifts between segments of the peripheral region are designed to be equal to the design wavelength or multiples of the design wavelength, the discontinuous peripheral region of the described refractive correctors is itself not designed to form a diffractive pattern generating distinct foci at different distances, and thus is not designed to provide multi-focality. Accordingly, in particular embodiments, the refractive corrector is designed to be mono-focal for a design wavelength of the refractive corrector. In further embodiments, however, further design features may be incorporated into the refractive corrector if desired to additionally provide multi-focality.

In various embodiments, at least one of the central zone or peripheral region of the refractive corrector may comprise materials of varying refractive index contributing to the wavefront cross-section phase profile, or may comprise materials of constant refractive index. More particularly, the wavefront cross-section phase profile in the central zone and peripheral region of the refractive corrector may be established by varying the thickness of a material of constant refractive index across the central zone and peripheral region, by varying the refractive index of the materials forming such central zone and peripheral region across such central zone and peripheral region, or by any combination of varying the thickness of the materials and the refractive index of the materials over each of the central zone and peripheral regions. In particular embodiments, the wavefront cross-section phase profile in the central zone and peripheral region of the refractive corrector is established at least in part by varying the refractive index of the materials forming at least one of such central zone and peripheral region across at least one of such central zone and peripheral region. In further embodiments, the wavefront cross-section phase profile in the central zone and peripheral region of the refractive corrector is established at least in part by varying the refractive index of the materials forming each of such central zone and peripheral region across each of such central zone and peripheral region.

In various embodiments, the central continuous zone and discontinuous peripheral region structures of the described refractive correctors can be applied to existing refracting structures such as contact lenses or IOLs with base power, or by direct writing into the human cornea using recently developed blue-femtosecond laser high repetition rate technology (see, e.g., "First Demonstration of Ocular Refractive Change Using Blue-IRIS in Live Cats," Investigative Ophthalmology and Visual Science, July 2014, Vol. 55:4603-4612, and U.S. Pat. Nos. 8,617,147, 8,486,055 and 8,512,320, the disclosures of which are incorporated herein by reference in their entireties), and further laser writing processes such as described in U.S. Pat. Nos. 6,450,642, 7,105,110, US 2008/0001320, US 2009/0287306, US 2009/0157178, US 2010/0228345, US 2012/0310340, and US 2012/0310223 referenced above, the disclosures of which are further incorporated herein by reference in their entireties. Alternatively, the described mixed continuous and discontinuous refractive corrector structures may be made by conventional molding or lathing and milling processes. Mixed continuous-discontinuous Fresnel-type lenses of the kinds described in this disclosure may find applications outside the field of ophthalmology as well.

In particular embodiments, the wavefront cross-section phase profile in the central zone and peripheral region of the refractive corrector is established at least in part by laser machining the refractive corrector (or by direct writing into the human cornea) employing any of the laser-writing techniques referenced above, as wavefront cross-section profiles as described herein have the advantage of reducing the time to write an equivalent totally continuous wavefront cross-section profile in a refractive corrector, while providing lower scatter and improved vision correction in comparison to complete modulo-2n phase shift profiles written across the entire refractive corrector phase profile. More particularly, it is especially advantageous when laser writing a wavefront cross-section profile to vary the refractive index of the materials forming at least one of such central zone and peripheral region across at least one of such central zone and peripheral region, and further when laser writing a wavefront cross-section phase profile to vary the refractive index of the materials forming each of such central zone and peripheral region across each of such central zone and peripheral region.

In particular embodiments, the refractive corrector wavefront cross-section profile may be formed by irradiating an optical, polymeric material, or by direct writing into the human cornea, with very short laser pulses of light as described in U.S. Publication Nos. 2008/0001320, 2009/0287306, 2012/0310340 and 2012/0310223 incorporated by reference above, where such short laser pulses are of sufficient energy such that the intensity of light within the focal volume will cause a nonlinear absorption of photons (typically multi-photon absorption) and lead to a change in the refractive index of the material within the focal volume, while the material just outside of the focal volume will be minimally affected by the laser light. The femtosecond laser pulse sequence pertaining to an illustrative embodiment, e.g., operates at a high repetition-rate, e.g., 80 MHz, and consequently the thermal diffusion time (>0.1 µs) is much longer than the time interval between adjacent laser pulses (~11 ns). Under such conditions, absorbed laser energy can accumulate within the focal volume and increase the local temperature. This thermal mechanism likely plays a role in the formation of laser-induced refractive structures in optical, polymeric materials. Moreover, the presence of water in the polymeric material is believed to advantageously influence the formation of the refractive structures. As such, optical hydrogel polymers provide much greater processing flexibility in the formation of the refractive structures as compared to zero or low water content optical polymers, e.g., the hydrophobic acrylates or low-water (1% to 5% water content) acrylate materials. The irradiated regions exhibit little or no scattering loss, which means that the resulting refractive structures that form in the focal volume are not clearly visible under appropriate magnification without phase contrast enhancement. In other words, the refractive structures are virtually transparent to the human eye without some form of image enhancement. An optical material is a polymeric material that permits the transmissions of at least 80% of visible light through the material, that is, an optical material does not appreciably scatter or block visible light.

According to one specific embodiment, a refractive corrector is formed by providing an optical, polymeric lens material having an anterior surface and posterior surface and an optical axis intersecting the surfaces; and forming at least one laser-modified layer disposed between the anterior surface and the posterior surface with light pulses from a laser by scanning the light pulses along regions of the optical, polymeric material to cause changes in the refractive index of the polymeric lens material, so that the optical, polymeric lens material comprises (a) a central zone having a continuous wavefront cross-section phase profile, having a wavefront maximum height of greater than 1 design wavelength λ in the area of the central zone, and (b) a peripheral region comprising multiple segments and having a discontinuous wavefront cross-section phase profile having phase shifts between segments that are equal to the design wavelength or multiples of the design wavelength, wherein the phase shifts in the peripheral region are less than or equal to the wavefront maximum height in the central zone. In such embodiment, the at least one laser-modified layer forms at least part of at least one of the central zone or the peripheral region.

According to another embodiment, a refractive property of ocular tissue in an eye is modified by forming at least one optically-modified layer in at least one of the corneal stroma and the crystalline lens ocular tissue in an eye by scanning light pulses from a laser focused in the corneal stroma or crystalline lens ocular tissue along regions of the corneal stroma or crystalline lens ocular tissue to cause changes in the refractive index within the ocular tissue to form a modified corneal stroma or crystalline lens, so that the modified corneal stroma or crystalline lens comprises (a) a central zone having a continuous wavefront cross-section phase profile, having a wavefront maximum height of greater than 1 design wavelength λ in the area of the central zone, and (b) a peripheral region comprising multiple segments and having a discontinuous wavefront cross-section phase profile having phase shifts between segments that are equal to the design wavelength or multiples of the design wavelength, wherein the phase shifts in the peripheral region are less than or equal to the wavefront maximum height in the central zone. In such embodiment, the at least one optically-modified layer forms at least part of at least one of the central zone or the peripheral region.

Femtosecond laser pulse writing methods may be more advantageously carried out if an optical polymeric material, such as, e.g., an optical hydrogel material, includes a photosensitizer, as more particularly taught in U.S. Publication Nos. 2009/0287306 and 2012/0310340 incorporated by reference above. The presence of the photosensitizer permits one to set a scan rate to a value that is at least fifty times greater, or at least 100 times greater, than a scan rate without a photosensitizer present in the material, and yet provide similar refractive structures in terms of the observed change in refractive index of the material in the focal volume. Alternatively, the photosensitizer in the polymeric material permits one to set an average laser power to a value that is at least two times less, more particularly up to four times less, than an average laser power without a photosensitizer in the material, yet provide similar refractive structures. A photosensitizer having a chromophore with a relatively large multi-photon absorption cross section is believed to capture the light radiation (photons) with greater efficiency and then transfer that energy to the optical polymeric material within the focal volume. The transferred energy leads to the formation of the refractive structures and the observed change in the refractive index of the material in the focal volume.

A 60×0.70NA Olympus LUCPlanFLN long-working-distance microscope objective with variable spherical aberration compensation may be employed to laser-write refractive segments. As indicated by the following equation $$\Delta T(r, z, t = 0) = \frac{\beta \tau_P [I(0, 0)]^2 \exp\left[-4\left(\frac{r^2}{a^2} + \frac{z^2}{b^2}\right)\right]}{c_p \rho}$$

the localized instantaneous temperature depends on both the pulse intensity and the magnitude of the two-photon absorption (TPA) coefficient. In order to produce an optical modification of a material that is of purely refractive character, i.e., non-absorbing or scattering, it is important to avoid optical damage, i.e., observed burning (scorching) or carbonization of the polymeric material. Such material or optical damage can be caused by excitation intensities exceeding a critical free-electron density. For hydrogel polymers containing a fair amount of water, the optical breakdown threshold is much lower than that in silica glasses. This breakdown threshold limits the pulse energy (in many cases to approximately 0.1 nJ to 20 nJ) that the hydrogel polymers can tolerate, and yet provide the observed changes in the refractive index within the focal volume.

Another way to increase energy absorption at a given intensity level is to increase the nonlinear absorption coefficient β by doping the optical, polymeric material with a particular chromophore and tuning the short pulse laser near a two-photon transition of the chromophore. In this regard, optical, hydrogel materials doped with a non-polymerizable photosensitizer or a polymerizable photosensitizer have been prepared. The photosensitizer will include a chromophore having a two-photon, absorption cross-section of at least 10 GM between a laser wavelength range of 750 nm to 1100 nm. In the former case of a non-polymerizable photosensitizer, solutions containing a photosensitizer may be prepared and the optical, hydrogel polymeric materials may be allowed to come in contact with such solutions to allow up-take of the photosensitizer into the polymeric matrix of the polymer. In the later case of a polymerizable photosensitizer, monomers containing a chromophore, e.g., a fluorescein-based monomer, may be used in the monomer mixture used to form the optical, polymeric material such that the chromophore becomes part of the polymeric matrix. Further, one could easily use a solution containing a non-polymerizable photosensitizer to dope an optical, polymeric material that had been prepared with a polymerizable photosensitizer. Also, it is to be understood that the chromophoric entities could be the same or different in each respective photosensitizer.

The concentration of a polymerizable, monomeric photosensitizer having a two-photon, chromophore in an optical material, preferably an optical, hydrogel material, can be as low as 0.05 wt. % and as high as 10 wt. %. Exemplary concentration ranges of polymerizable monomer having a two-photon, chromophore in an optical, hydrogel material is from 0.1 wt. % to 6 wt. %, 0.1 wt. % to 4 wt. %, and 0.2 wt. % to 3 wt. %. In various aspects, the concentration range of polymerizable monomer photosensitizer having a two-photon, chromophore in an optical, hydrogel material is from 0.4 wt. % to 2.5 wt. %.

Due to the high repetition rate pulse sequence used in the irradiation process, the accumulated focal temperature increase can be much larger than the temperature increase induced by a single laser pulse. The accumulated temperature increases until the absorbed power and the dissipated power are in dynamic balance. For hydrogel polymers, thermal-induced additional crosslinking within the polymer network can produce a change in the refractive index as the local temperature exceeds a transition temperature. If the temperature increase exceeds a second threshold, a somewhat higher temperature than the transition temperature, the polymer is pyrolytically degraded and carbonized residue and water bubbles are observed. In other words, the material exhibits visible optical damage (scorching). Each of the following experimental parameters such as laser repetition rate, laser wavelength and pulse energy, TPA coefficient, and water concentration of the materials should be considered so that a desired change in the refractive index can be induced in the hydrogel polymers without optical damage.

The pulse energy and the average power of the laser, and the rate at which the irradiated regions are scanned, will in-part depend on the type of polymeric material that is being irradiated, how much of a change in refractive index is desired and the type of refractive structures one wants to create within the material. The selected pulse energy will also depend upon the scan rate and the average power of the laser at which the refractive structures are written into the polymer material. Typically, greater pulse energies will be needed for greater scan rates and lower laser power. For example, some materials will call for a pulse energy from 0.05 nJ to 100 nJ or from 0.2 nJ to 10 nJ.

Within the stated pulse energies above, the optical, hydrogel polymeric material may be irradiated at a scan rate of, e.g., at least 0.1 mm/s, from 0.1 mm/s to 10 mm/s or from 0.4 mm/s to 4 mm/s.

Within the stated pulse energies and scan rates above, the average laser power used in the irradiation process may be, e.g., from 10 mW to 400 mW, or from 40 mW to 220 mW.

In one embodiment, the average pulse energy may be from 0.2 nJ to 10 nJ and the average laser power may be from 40 mW to 220 mW. The laser also operates within a wavelength of 650 nm to 950 nm. Within the stated laser operating powers, the optical, hydrogel polymeric material is irradiated at a scan rate, e.g., of from 0.4 mm/s to 4 mm/s.

A photosensitizer will include a chromophore in which there is little or no intrinsic linear absorption in the spectral range of 600-1000 nm. The photosensitizer is present in the optical, hydrogel polymeric material to enhance the photo-efficiency of the two-photon absorption required for the formation of the described refractive structures. Photosensitizers of particular interest include, but are not limited to, the following compounds. The compounds below are merely exemplary.

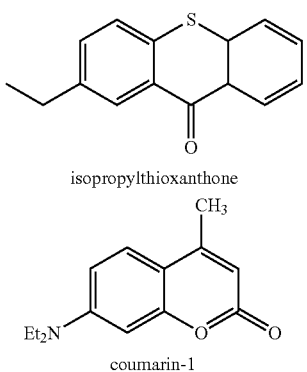

isopropylthioxanthone coumarin-1

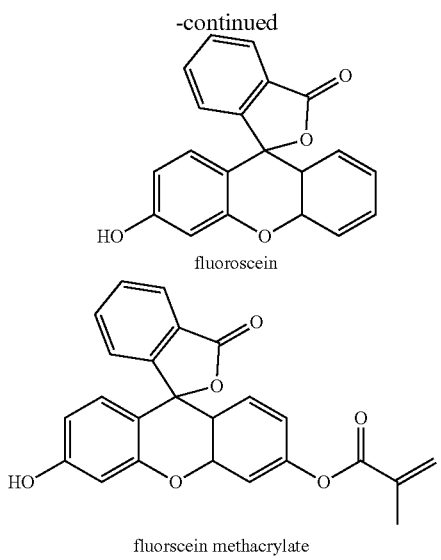

fluoroscein fluorscein methacrylate

As described in U.S. Publication Nos. 2009/0287306 and 2012/0310340 in greater detail in the Example sections, a commercial IOL material, Akreos®, presently marketed by Bausch & Lomb, was subjected to laser irradiation according to the processes described therein. An Akreos® IOL is a HEMA-based, hydrogel material with 26% to 28% water content. The micromachining process was used to imprint refractive structures in an Akreos® IOL without photosensitizer and an Akreos® IOL doped with a solution containing 17 wt. % coumarin-1. The irradiation experiments were conducted with both dry and hydrated materials. The refractive structures formed only in the hydrated materials. In brief, the magnitude of the measured change in refractive index was at least ten times greater in the Akreos® IOL doped with the coumarin solution at a given scan rate and an average laser power than the Akreos® IOL without the coumarin.

In another illustrative aspect described in U.S. Publication Nos. 2009/0287306 and 2012/0310340, a balafilcon A silicone hydrogel was prepared by adding fluorescein monomer (0.17% by weight) as a polymerizable photosensitizer to the polymer monomer mixture. The balafilcon A doped with fluorescein was then subjected to laser radiation according to the processes described therein. Again, the described irradiation process was used to imprint refractive structures in the silicone hydrogel without photosensitizer and the silicone hydrogel doped with 0.17 wt. % fluorescein monomer. Again, experiments were conducted with both dry and hydrated materials, and again, the refractive structures formed only in the hydrated materials. In brief, the magnitude of the measured change in refractive index was at least ten times greater in the balafilcon A silicone hydrogel doped with 0.17 wt. % fluorescein monomer at an average laser power of 60 mW than balafilcon A without the photosensitizer. This 10-fold difference in change in refractive index was observed even with a 10-fold increase in scan rate in the photosensitized material; i.e., 0.5 mm/s in the undoped material and 5.0 mm/s in the photosensitized material.

The laser may generate light with a wavelength in the range from violet to near-infrared. In various aspects, the wavelength of the laser may be in the range from 400 nm to 1500 nm, from 400 nm to 1200 nm, or from 650 nm to 950 nm.

In an exemplary aspect, the laser may be a pumped Ti:sapphire laser with an average power of 10 mW to 1000 mW. Such a laser system will generate light with a wavelength of approximately 800 nm. In another exemplary aspect, an amplified fiber laser that can generate light with a wavelength from 1000 nm to 1600 nm may be used.

The laser may have a peak intensity at focus of greater than $10^{13}$ W/cm$^2$. At times, it may be advantageous to provide a laser with a peak intensity at focus of greater than $10^{14}$ W/cm$^2$, or greater than $10^{15}$ W/cm$^2$.

The ability to form refractive structures in optical polymeric materials provides an important opportunity to an ophthalmic surgeon or practitioner to modify the refractive index of an optical device, e.g., an intraocular lens or corneal inlay, following implantation of the device into an eye of a patient. The method allows the surgeon to correct aberrations as a result of the surgery. The method also allows the surgeon to adjust the refractive properties of the lens or inlay by adjusting the refractive index in the irradiated regions based on the vision correction required of each patient. For example, starting from a lens of selected power (will vary according to the ocular requirements of the patient), the surgeon can further adjust the refractive properties of the lens to correct a patient's vision based upon the individual needs of the patient. In essence, an intraocular lens would essentially function like a contact lens or glasses to individually correct for the refractive error of a patient's eye. Moreover, because the implanted lens can be adjusted by adjusting the refractive index of select regions of the lens, post-operative refractive errors resulting from pre-operative measurement errors, variable lens positioning during implantation, and wound healing (aberrations) can be corrected or fine tuned in-situ.

Typically, the irradiated portions of the optical, hydrogel polymeric material will exhibit a positive change in refractive index of about 0.01 or more. In one embodiment, the refractive index of the region will increase by about 0.03 or more. As disclosed in U.S. Publication Nos. 2009/0287306 and 2012/0310340, a positive change in refractive index in a hydrated, Akreos® IOL material of about 0.06 has been measured.

In an exemplary aspect, the irradiated regions of an optical, polymeric material can be defined by two- or three-dimensional structures providing the desired wavefront cross-section profile. The two- or three-dimensional structures can comprise an array of discrete cylinders, a series of lines, or a combination of an array of cylinders and a series of lines. Moreover, the two- or three-dimensional structures can comprise area or volume filled structures, respectively. These area or volume filled structures can be formed by continuously scanning the laser at a constant or varying scan rate over a selected region of the polymeric material. Nanometer-sized structures can also be formed by the zone-plate-array lithography method describe by R. Menon et al., *Proc. SPIE*, Vol. 5751, 330-339 (May 2005); *Materials Today*, p. 26 (February 2005).

In one aspect, the refractive structures may be formed proximate to the top anterior surface of an intraocular lens. For example, a positive or negative lens element (three-dimensional) is formed within a 300 µm volume, or within a 100 µm volume, from the anterior surface of the lens. The term "anterior surface" is the surface of the lens that faces the anterior chamber of a human eye.

Figure 2:
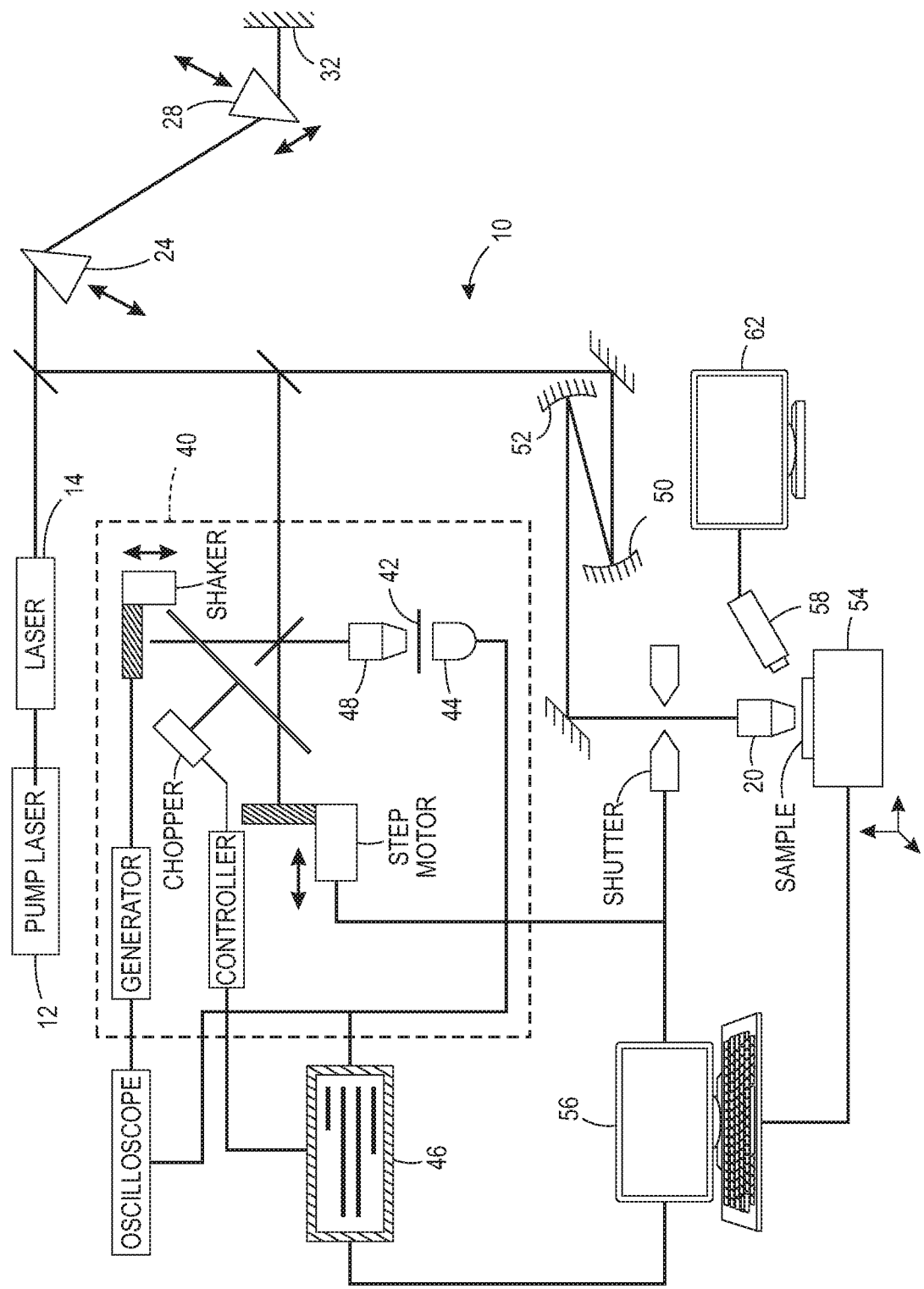
FIG. 2 is a schematic of a laser system which may be used for writing a wavefront cross-section phase profile in a refractive corrector in accordance with an embodiment.

A non-limiting embodiment of a laser system 10 which may be used for irradiating an optical, polymeric material with a laser to modify the refractive index of the material in select regions to form a refractive corrector having a wavefront cross-section phase profile as described herein is illustrated in FIG. 2. A laser source comprises a Kerr-lens mode-locked Ti:Sapphire laser 12 (Kapteyn-Murnane Labs, Boulder, Colo.) pumped by 4 W of a frequency-doubled Nd:YVO4 laser 14. The laser generates pulses of 300 mW average power, 30 fs pulse width, and 93 MHz repetition rate at wavelength of 800 nm. Because there is a reflective power loss from the mirrors and prisms in the optical path, and in particular from the power loss of the objective 20, the measured average laser power at the objective focus on the material is about 120 mW, which indicates the pulse energy for the femtosecond laser is about 1.3 nJ.

Due to the limited laser pulse energy at the objective focus, the pulse width must be preserved so that the pulse peak power is strong enough to exceed the nonlinear absorption threshold of the materials. Because a large amount of glass inside the focusing objective significantly increases the pulse width due to the positive dispersion inside of the glass, an extra-cavity compensation scheme is used to provide the negative dispersion that compensates for the positive dispersion introduced by the focusing objective. Two SF10 prisms 24 and 28 and one ending mirror 32 form a two-pass, one-prism-pair configuration. In a particular instance, a 37.5 cm separation distance between the prisms is used to compensate for the positive dispersion of the microscope objective and other optics within the optical path.

A collinear autocorrelator 40 using third-order harmonic generation is used to measure the pulse width at the objective focus. Both $2^{nd}$ and $3^{rd}$ harmonic generation have been used in autocorrelation measurements for low NA or high NA objectives. Third-order surface harmonic generation (THG) autocorrelation may be used to characterize the pulse width at the focus of the high-numerical aperture (NA) objectives because of its simplicity, high signal to noise ratio, and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, a transform-limited 27 fs duration pulse is used, which is focused by a 60×0.70NA Olympus LUCPlanFLN long-working-distance objective 48.

Because the laser beam will spatially diverge after it comes out of the laser, a concave mirror pair 50 and 52 is added into the optical path in order to adjust the dimension of the laser beam so that the laser beam can optimally fill the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micromachine different patterns in the materials using different scanning speeds at different position or depth in the optical material, and different laser exposure times. In addition, a CCD camera 58 along with a monitor 62 is used beside the objective 20 to monitor the process in real time.

The method and optical apparatus described above can be used to modify the refractive index of an intraocular lens following the surgical implantation of the intraocular lens in a human eye (or before the lens is implanted in an eye).

Accordingly, an embodiment described herein is directed to a method comprising identifying and measuring the aberrations resulting from the surgical procedure of providing a patient with an IOL. Once the aberrations are identified and quantified using methods well known in the art of ophthalmology, this information is processed by a computer. Of course, information related to the requisite vision correction for each patient can also be identified and determined, and this information can also be processed by a computer. There are a number of commercially available diagnostic systems that are used to measure the aberrations. For example, common wavefront sensors used today are based on the Schemers disk, the Shack Hartmann wavefront sensor, the Hartmann screen, and the Fizeau, and Twyman-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the refractive structures to be written into the lens material to correct for those aberrations or to provide vision correction to the patient. These computer programs are well known to those of ordinary skill in the art. The computer then communicates with the laser-optical system and select regions of the lens are irradiated with a laser having a pulse energy from 0.05 nJ to 1000 nJ as described herein, to provide a wavefront cross-section phase profile comprising a central zone and peripheral region in accordance with the present invention.

The optical, hydrogel polymeric materials that can be irradiated with a laser according to the methods described to form refractive correctors in accordance with various embodiments can be any optical, hydrogel polymeric material known to those of ordinary skill in the polymeric lens art, particularly those in the art familiar with optical polymeric materials used to make intraocular lenses. Non-limiting examples of such materials include those used in the manufacture of ophthalmic devices, such as siloxy-containing polymers, acrylic, hydrophilic or hydrophobic polymers or copolymers thereof. The forming of the refractive structures is particularly suited for modifying the refractive index in select and distinct regions of a polymeric, optical silicone hydrogel, or a polymeric, optical non-silicone hydrogel.

The term "hydrogel" refers to an optical, polymeric material that can absorb greater than 10% by weight water based on the total hydrated weight. In fact, many of the optical, hydrogel polymeric materials will have a water content greater than 15% or greater than 20%. For example, many of the optical, hydrogel polymeric materials will have a water content from 15% to 60% or from 15% to 40%.

The optical, hydrogel polymeric materials are of sufficient optical clarity, and will have a relatively high refractive index of approximately 1.40 or greater, particularly 1.48 or greater. Many of these materials are also characterized by a relatively high elongation of approximately 80 percent or greater.

In one embodiment, the optical polymeric materials are prepared as a copolymer from at least three monomeric components. The first monomeric component, preferably a monomeric component with aromatic functionality, is present in the copolymer in an amount of at least 60% by weight, and its homopolymer will have a refractive index of at least 1.50, particularly at least 1.52 or at least 1.54. The second monomeric component, preferably, an alkyl(meth)acrylate, is present in the copolymer in an amount from 3% to 20% or from 3% to 10%, by weight. The first and second monomeric components together represent at least 70% by weight of the copolymer. The term "homopolymer" refers to a polymer that is derived substantially completely from the respective monomeric component. Minor amounts of catalysts, initiators, and the like can be included, as is conventionally the case, in order to facilitate the formation of the homopolymer.

Particularly useful first monomeric components include styrene, vinyl carbazole, vinyl naphthalene, benzyl(meth)acrylate, phenyl(meth)acrylate, naphthyl(meth)acrylate, 2-phenoxyethyl(meth)acrylate, 2,3-dibromopropyl-(meth) acrylate and any one mixture thereof. Particularly useful second monomeric components include n-butyl(meth)acrylate, n-hexyl(meth)acrylate, 2-ethylhexyl-(meth)acrylate, 2-ethoxyethyl(meth)acrylate, 2,3-dibromopropyl(meth) acrylate, 1,1-dihydroperfluorobutyl(meth)acrylate and any one mixture thereof.

The third monomeric component is a hydrophilic monomeric component. The hydrophilic component is present in an amount, from 2% to 30% by weight of the copolymer. The hydrophilic component is particularly present in an amount of less than about 20% by weight of the copolymer. Copolymers that include about 10% by weight or more of a hydrophilic monomeric component tend to form hydrogels if placed in an aqueous environment. The term "hydrophilic monomeric component" refers to compounds that produce hydrogel-forming homopolymers, that is, homopolymers which become associated with at least 25% of water, based on the weight of the homopolymer, if placed in contact with an aqueous solution.

Specific examples of useful hydrophilic monomeric components include N-vinyl pyrrolidone; hydroxyalkyl (meth) acrylates such as 2-hydroxyethyl (meth)acrylate, 3-hydroxypropyl (meth)acrylate, 2-hydroxypropyl (meth)acrylate, 4-hydroxybutyl (meth)acrylate, 2,3-dihydroxypropyl (meth) acrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and any one mixture thereof.

In another embodiment, the optical polymeric materials are prepared as a copolymer from at least two monomeric components and a photosensitizer. The photosensitizer can be polymerizable or be entrapped within the formed polymer. The first monomeric component is a hydrophilic monomeric component. The hydrophilic component is present in an amount from 50% to 90% by weight of the copolymer. The hydrophilic component is particularly present in an amount of 60% to 85% by weight of the copolymer. The second monomeric component, preferably, an alkyl(meth) acrylate, is present in the copolymer in an amount from 5% to 20% or from 3% to 10%, by weight. The first and second monomeric components together represent at least 90% by weight of the copolymer.

The polymeric optical materials will likely include a crosslink component that can form crosslinks with at least the first or the second monomeric components. Advantageously, the crosslink component is multi-functional and can chemically react with both the first and second monomeric components. The crosslink component is often present in a minor amount relative to the amounts of the first and second monomeric components. Particularly, the crosslink component is present in a copolymer in an amount of less than about 1% by weight of the copolymer. Examples of useful crosslink components include ethylene glycol dimethacrylate, propylene glycol dimethacrylate, ethylene glycol diacrylate and the like and mixtures thereof.

In one aspect, the optical, polymeric materials can be prepared from one or more aromatic (meth)acrylate monomers having the formula:

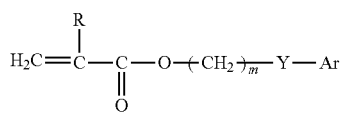

wherein: R is H or $CH_3$; m is an integer selected from 0 to 10; Y is nothing, O, S, or $NR^1$, wherein $R^1$ is H, $CH_3$, $C_2$-$C_6$ alkyl, iso-$OC_3H_7$, phenyl or benzyl; Ar is any aromatic ring, e.g., phenyl, which can be unsubstituted or substituted with H, $CH_3$, $C_2H_5$, n-$C_3H_7$, iso-$C_3H_7$, $OCH_3$, $C_6H_{11}$, Cl, Br, phenyl or benzyl; and a crosslinking component.

Exemplary aromatic (meth)acrylate monomers include, but are not limited to: 2-ethylphenoxy (meth)acrylate, 2-ethylthiophenyl (meth)acrylate, 2-ethylaminophenyl (meth)acrylate, phenyl-(meth)acrylate, benzyl (meth)acrylate, 2-phenylethyl (meth)acrylate, 3-phenylpropyl-(meth)acrylate, 4-phenylbutyl (meth)acrylate, 4-methylphenyl (meth)acrylate, 4-methylbenzyl (meth)acrylate, 2-2-methylphenylethyl (meth)acrylate, 2-3-methylphenylethyl (meth)acrylate, 2-4-methylphenylethyl (meth)acrylate, 2-(4-propylphenyl)ethyl (meth)acrylate, 2-(4-(1-methylethyl)phenyl)ethyl methacrylate, 2-(4-methoxyphenyl)ethyl methacrylate and the like.

Generally, if the optical, polymeric material is prepared with both an aromatic acrylate and an aromatic methacrylate as defined by the formula above, the materials will generally comprise a greater mole percent of aryl acrylate ester residues than of aryl methacrylate ester residues. It is preferred that the aryl acrylate monomers constitute from about 20 mole percent to about 60 mole percent of the polymer, while the aryl methacrylate monomers constitute from about 5 mole percent to about 20 mole percent of the polymer. Most advantageous is a polymer comprising about 30-40 mole percent 2-phenylethyl acrylate and about 10-20 mole percent 2-phenylethyl methacrylate. Hydrophilic monomer is also present in about 20-40 mol percent.

In another aspect, the optical, polymeric materials will have a fully hydrated (equilibrium) water content from 5% to 15% by weight, which also helps to minimize the degree of hazing following thermal stress as described, as well as minimize the formation of water vacuoles in-vivo. To achieve the desired water content, one may include a hydrophilic, aromatic monomer having a formula, G-D-Ar, wherein Ar is a $C_6$-$C_{14}$ aromatic group having a hydrophilic substituent, in the polymerizable compositions. D is a divalent linking group, and G is a polymerizable ethylenic site.

One particular hydrophilic aromatic monomer is represented by the formula

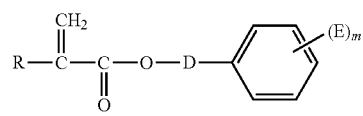

wherein R is hydrogen or $CH_3$; D is a divalent group selected from the group consisting of straight or branched $C_1$-$C_{10}$ hydrocarbons and an alkyleneoxide (e.g., —($CH_2CH_2O)_n$—), and E is selected from the group consisting of hydrogen (if D is alkyleneoxide), carboxy, carboxamide, and monohydric and polyhydric alcohol substituents. Exemplary hydrophilic substituents include, but are not limited to, —COOH, —$CH_2$—$CH_2OH$, —(CHOH)$_2$ $CH_2OH$, —$CH_2$—CHOH—$CH_2OH$, poly(alkylene glycol), —C(O)O—$NH_2$ and —C(O)—N(CH$_3$)$_2$.

Exemplary hydrophilic, aromatic monomers are represented by the following

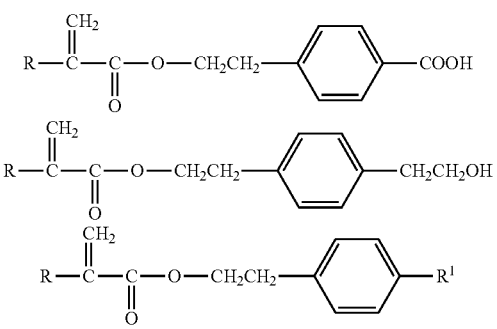

wherein R is hydrogen or $CH_3$ and $R^1$ is —C(O)O—$NH_2$ or —C(O)—N(CH$_3$)$_2$.

In another aspect, the optical, polymeric material is prepared from a first aromatic monomeric component, which is present in 5-25% by weight, the second monomeric component is a hydrophilic monomeric component, e.g., 2-hydroxyethyl (meth)acrylate, which is present from 30 to 70% by weight; and 5 to 45% by weight of a another alkyl (meth)acrylate selected from the group consisting of methyl (meth)acrylate, ethyl (meth)acrylate, propyl (meth)acrylate, butyl (meth)acrylate, pentyl (meth)acrylate, hexyl meth)acrylate, heptyl (meth)acrylate, nonyl (meth)acrylate, stearyl meth)acrylate, octyl (meth)acrylate, decyl (meth)acrylate, lauryl (meth)acrylate, pentadecyl (meth)acrylate and 2-ethylhexyl (meth)acrylate. Among the alkyl (meth)acrylates, those containing 1 to 3 carbon atoms of alkyl group are particularly advantageous.

Exemplary aromatic monomeric components include ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenylethyl methacrylate, 2-(4-propylphenyl)ethyl methacrylate, 2-(4-(1-methylethyl)pheny)ethyl methacrylate, 2-(4-methoxyphenyl)ethylmethacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mixtures thereof. EGPEA and polyEGPEA are two of the more preferred first monomeric components.

In another aspect, the optical, polymeric material is prepared from a hydrophilic acrylic that comprises about 90% (by weight) N-vinylpyrrolidone (NVP) and about 10% (by weight) 4-t-butyl-2-hydroxycyclohexyl methacrylate. This methacrylate hydrogel can absorb about 80% (by weight) water because of the high percentage of NVP. Its refractive index when hydrated is very close to the index of water. Another hydrophilic acrylic of interest is referred to as HEMA B, which is a poly(2-hydroxyethyl methacrylate) cross-linked with about 0.9% (by weight) of ethylene glycol dimethacrylate ("EGDMA"). This HEMA-hydrogel can absorb about 37% (by weight) water.

One particular hydrophilic, acrylic material of interest is based upon a commercially available IOL sold in the market by Bausch & Lomb under the trade name Akreos®. This acrylic material comprises about 80% by weight HEMA and 20 wt % MMA.

The optical, polymeric material can also be prepared by copolymerizing a specific monomer mixture comprising perfluorooctylethyloxypropylene (meth)acrylate, 2-phenylethyl (meth)acrylate, an alkyl (meth)acrylate monomer having the following general formula,

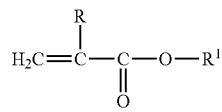

wherein R is hydrogen or methyl and $R^1$ is a linear or branched $C_4$-$C_{12}$ alkyl group, hydrophilic monomer and a crosslinking monomer. An exemplary list of alkyl (meth) acrylate monomer include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The perfluorooctylethyloxypropylene (meth)acrylate is present from 5% to 20% by weight, the 2-phenylethyl (meth)acrylate is present from 20% to 40% by weight, the alkyl (meth)acrylate monomer is present from 20% to 40% by weight, the hydrophilic monomer is present from 20% to 35%, and the crosslinking agent is present from 0.5% to 2% by weight.

The optical, polymeric component will likely include a crosslinking agent. The copolymerizable crosslinking agent(s) useful in forming the copolymeric material include any terminally ethylenically unsaturated compound having more than one unsaturated group. Particularly, the crosslinking agent includes a diacrylate or a dimethacrylate. The crosslinking agent may also include compounds having at least two (meth)acrylate and/or vinyl groups. Particularly advantageous crosslinking agents include diacrylate compounds.

The optical, polymeric materials are prepared by generally conventional polymerization methods from the respective monomeric components. A polymerization mixture of the monomers in the selected amounts is prepared and a conventional thermal free-radical initiator is added. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butylcyclohexyl) peroxydicarbonate, azonitriles, such as azobisisobytyronitrile, and the like. A particular initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

Without exclusion as to any lens materials or material modifications, e.g., the inclusion of a photosensitizer, or laser parameters described herein above, the foregoing disclosed techniques and apparatus can be used to modify the refractive properties, and thus, the dioptric power, of an optical polymeric material, typically, an optical hydrogel material, in the form of, but not limited to, an IOL or corneal inlay, by creating (or machining) a refractive structure with a gradient index in one, two or three dimensions of the optical material, as more fully described in U.S. Publication Nos. 2012/0310340 and 2012/0310223, incorporated by reference above. The gradient refractive structure can be formed by continuously scanning a continuous stream of femtosecond laser pulses having a controlled focal volume in and along at least one continuous segment (scan line) in the optical material while varying the scan speed and/or the average laser power, which creates a gradient refractive index in the polymer along the segment. Accordingly, rather than creating discrete, individual, or even grouped or clustered, adjoining segments of refractive structures with a constant change in the index of refraction in the material, a gradient refractive index is created within the refractive structure, and thereby in the optical material, by continuously scanning a continuous stream of pulses. As described in greater detail in U.S. Publication No. 2012/0310340, since the refractive modification in the material arises from a multiphoton absorption process, a well-controlled focal volume corrected for spherical (and other) aberrations will produce a segment having consistent and, if desired, constant depth over the length of the scan. As further noted, when a tightly focused laser beam consisting of femtosecond pulses at high repetition rate impinges on a material that is nominally transparent at the incident laser wavelength, there is little if any effect on the material away from the focal region. In the focal region, however, the intensity can exceed one terawatt per square centimeter, and the possibility of absorbing two or more photons simultaneously can become significant. In particular, the amount of two-photon absorption can be adjusted by doping or otherwise including in the irradiated material with selected chromophores that exhibit large two-photon absorption cross-section at the proper wavelength (e.g., between 750 nm and 1100 nm), which can significantly increase the scanning speed as already described. Also, multiple segments can be written into the material in a layer using different scan speeds and/or different average laser power levels for various segments to create a gradient index profile across the layer, i.e., transverse to the scan direction. Further, multiple, spaced gradient index (GRIN) layers can be written into the material along the z-direction (i.e., generally the light propagation direction through the material) to provide a desired refractive change in the material that corrects for some, most, or all higher order aberrations of a patient's eye. Such abilities to write continuously varying gradient index layers are particularly advantageous in forming refractive correctors having wavefront cross-section profiles in accordance with embodiments of the present invention. For ophthalmic applications, it is of particular interest that GRIN refractive structures are low scattering (as discussed above) and are of high optical quality.

In an illustrative aspect disclosed in U.S. Publication No. 2012/0310340, a cylindrical lens structure with a one-dimensional quadratic gradient index was written in an optical, polymeric material with three GRIN layers each 5 µm thick, spaced by 10 µm in the z-direction (i.e., a layer of non-modified optical material having a thickness of about 5 µm to 7 µm was between each two adjacent GRIN layers).

The resulting cylindrical lens was designed to provide approximately 1 diopter of astigmatism uniform along the length of the device.

As further disclosed in U.S. publication No. 2012/0310223, incorporated by reference above, the femtosecond micromachining approach employed with hydrogel materials may be adapted to similarly carry out refractive correction in biological tissues by reducing the femtosecond laser pulse energies below the optical breakdown thresholds for such biological tissues, and gradient index layers may similarly be formed in such biological tissues by varying the scan rates and/or scan powers while maintaining pulse energies below such threshold energies. More particularly, refractive structures may be formed in a living eye by a method including (a) directing and focusing femtosecond laser pulses in the blue spectral region within a cornea or a lens of the living eye at an intensity high enough to change the refractive index of the cornea or lens within a focal region, but not high enough to damage the cornea or lens or to affect cornea or lens tissue outside of the focal region; and (b) scanning the laser pulses across a volume of the cornea or the lens to provide the focal region with refractive structures in the cornea or the lens. The refractive structures advantageously exhibit little or no scattering loss, which means that the structures are not clearly visible under appropriate magnification without contrast enhancement.

Figure 3:
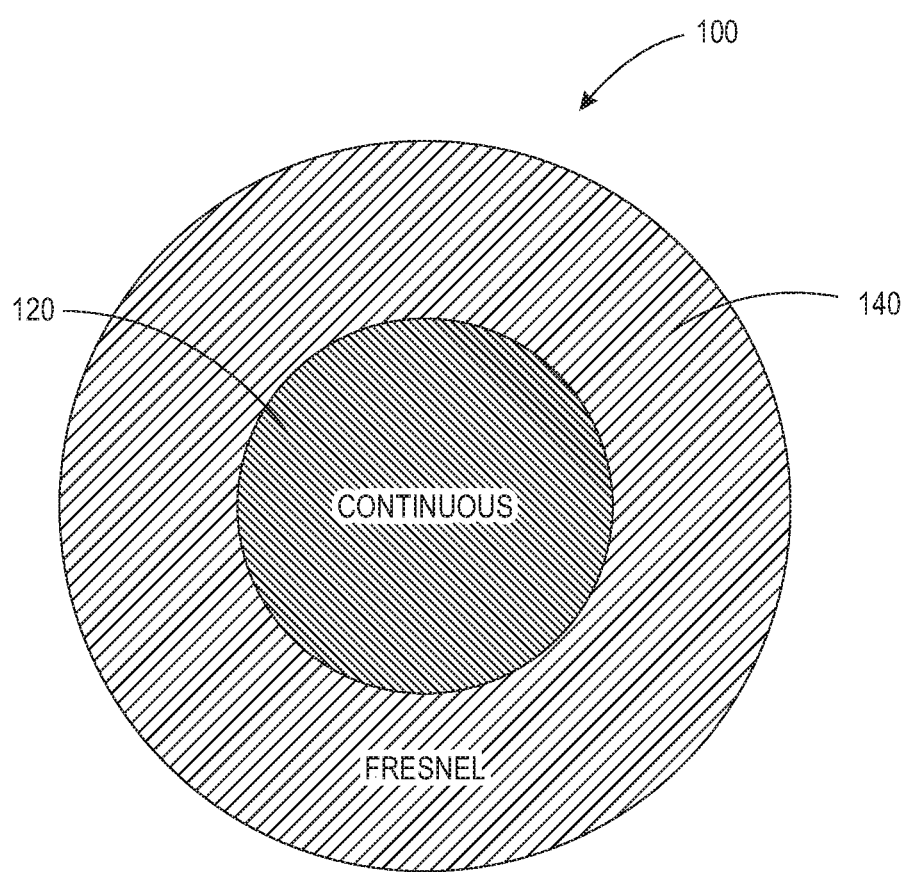
FIG. 3 schematically illustrates a hybrid continuous/Fresnel refractive corrector in accordance with an embodiment.

FIG. 3 shows a schematic representation of a refractive corrector in the form of a lens 100 having a central continuous refractive zone 120, and a peripheral Fresnel-type discontinuous phase shifting region 140. As shown in FIG. 3, the peripheral region may circumscribe the central zone, and more specifically an outer perimeter of the central zone and an outer perimeter of the peripheral region may be circular, where the optical axis of the lens is at the center of the circular regions. Lens 100 acts like a conventional refracting lens in the central zone, and as a Fresnel-type refractor in the peripheral region. In certain embodiments, the central zone may have an outer diameter of at least 10, at least 20, at least 25, or at least 30% of the outer diameter of the peripheral region, e.g., from 10% to 90%, from 20% to 80%, from 25% to 75%, or from 30% to 70% of the outer diameter of the peripheral region. Alternatively, in further embodiments, the central zone may comprise at least 20, at least 30, or at least 40% of the total area of the central zone and peripheral region combined, e.g., from 20% to 90%, from 30% to 85%, or from 40% to 80% of the total area of the central zone and peripheral region combined. The various embodiments thus provide a degree of freedom allowing one to choose a ratio of continuous refracting region to that of the discontinuous phase shift region, in order to provide desired visual acuity under specified conditions while still enabling reduced write times. In some specific embodiments, e.g., providing a central zone having an outer diameter of from 30% to 70% of the diameter of the peripheral region may provide optimal combined results. In certain embodiments, e.g., the central zone may have a diameter of from about 0.5 mm to about 5 mm, and the peripheral region may have an outer diameter of from about 3 mm to about 10 mm, while in other embodiments such diameters may be larger or smaller.

Example: Designs Incorporating a Parabolic Central Phase Shift Region

Figure 4A:
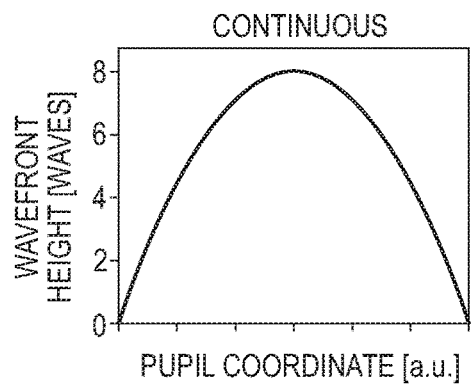
FIGS. 4a-4c schematically illustrate wavefront cross-sections of continuous, hybrid and Fresnel designs of parabolic phase shift refractive correctors.
Figure 4B:
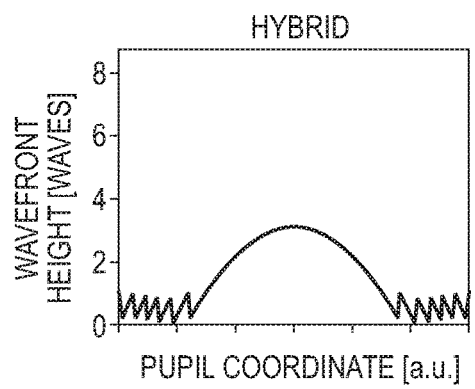
Figure 4C:
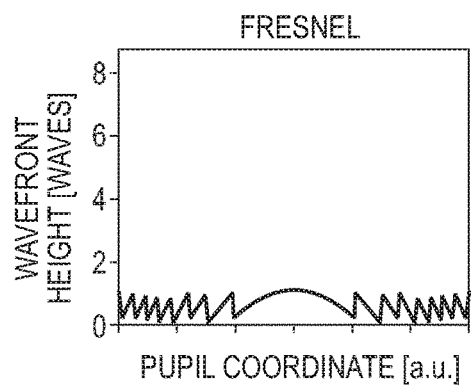

One particular design for a refractive corrector consists of a simple parabolic phase shift. As an illustrative example, wavefront cross-sections of (a) continuous, (b) hybrid continuous/Fresnel and (c) complete modulo $2\pi$ phase wrapped Fresnel designs are shown in FIGS. 4a, 4b and 4c, respectively. As the number of discrete steps in the wavefront decreases, these types of lenses become essentially conventional refracting structures with mostly continuous parabolic phase. Ultimately, for a fully continuous profile, the time taken to write such large peak phase shifts in the central zone may become prohibitive, thereby losing the advantage of the mixed continuous/Fresnel-type design.

Example: Retinal Image Quality of Mixed Continuous-Fresnel Type Lenses

Previously, the imaging quality of kinoform Fresnel lenses and chromatic effects have been considered ("Kinoform Lenses," J. A. Jordan, Jr., P. M. Hirsch, L. B. Lesem, and D. L. Van Rooy/Vol. 9, No. 8/Applied Optics 1887, (1970); "Binary Optics Technology: The Theory of Multi-Level Diffractive Optical Elements," G. J. Swanson, Technical Report 854, MIT Lincoln Laboratories (1989)). In the present case, we evaluate the effects of the mixed (or hybrid) continuous central zone/discontinuous peripheral Fresnel refractive corrector designs on human vision and visual performance.

Figure 5:
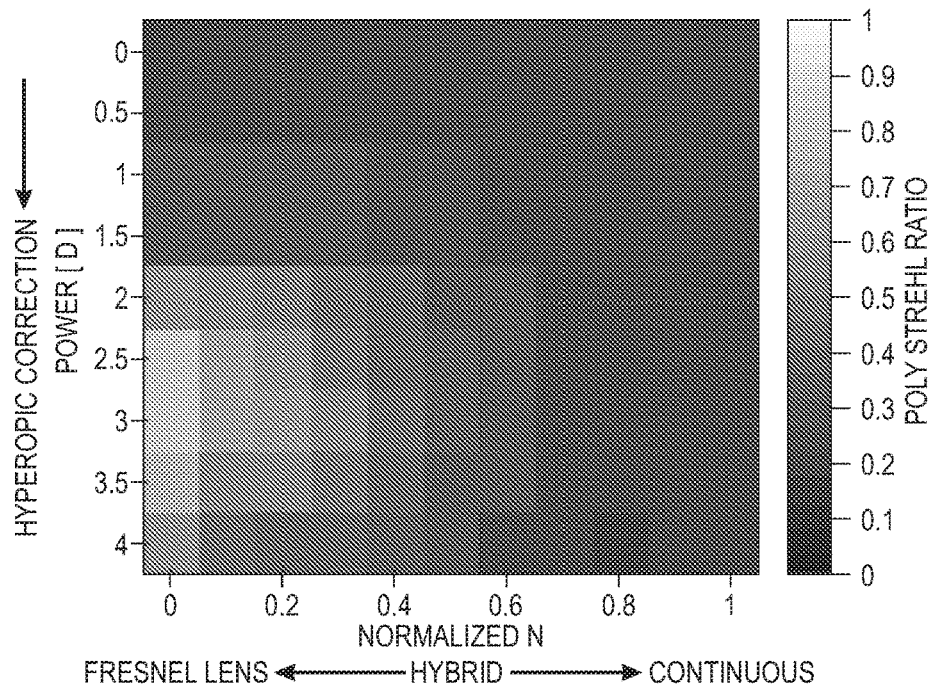
FIG. 5 illustrates calculated polychromatic retinal image quality for refractive correctors for a range of positive dioptric powers and degrees of mixed, continuous and Fresnel type phase profiles.

The average human eye suffers from a significant magnitude of longitudinal chromatic aberration ("Chromatic dispersions of the ocular media of human eyes." Atchison, David A., and George Smith. JOSA A 22.1: 29-37 (2005)), approximately 2 diopters over the visible spectrum (400-700 nm). Polychromatic retinal image quality was calculated for a range of positive dioptric powers and degrees of mixed continuous and Fresnel type phase profiles for simple parabolic phase shifts of the type illustrated in FIGS. 4a-4c, and the results are shown in FIG. 5, for the illustrative example of a 6 mm pupil.

The number of zones (of a phase height) in a conventional modulo $2\pi$ phase wrapped Fresnel design depends on the radius of the optical zone (R), wavelength ($\lambda$) and optical power in diopters (D) in accordance with the following formula:

$$\text{Number of Zones} = \text{ceiling}[R^2 * D/(2\lambda)]$$

The quantity "number of zones" is an integer, therefore we round up to the nearest integer, hence the "ceiling" function in the equation above. This equation comes from the definition of the Fresnel Number, which is defined as the number of zones with half a wave of phase, or $\pi$ radians. Therefore, the Fresnel number is twice the number of zones in a Fresnel lens.

In FIG. 5, N is the number of additional zones included in the central continuous region, relative to the number of zones in a conventional modulo $2\pi$ phase wrapped Fresnel design for a given dioptric power for a 6 mm lens. Therefore, for a pure Fresnel lens, N=0 because there are zero additional zones included in the central region. We normalize the min and max N values reported in FIG. 5 between 0 and 1, because there is a different maximum N value for lenses of different powers, as the larger the dioptric power of a lens, the more zones there are in a conventional Fresnel lens, and thus the higher the maximum N value. By normalizing N, the concept behind hybridization is easily communicated for all dioptric lens powers. Table I below, e.g., is an illustrative example showing the relationships between, N, normalized N, the radius of the inner continuous zone and the % of continuous central area of the entire lens for the case of 1 Diopter over a 6 mm diameter optical zone.

TABLE I

Lens Power = 1 D, 6 mm pupil diameter

| N | Normalized N | Lens Type | Outer Pupil Radius [mm] | Inner Continuous Region Radius [mm] | % Continuous Area of Max Aperture |
|---|---|---|---|---|---|
| 0 | 0.00 | Fresnel | 3.0 | 1.0 | 12% |
| 1 | 0.14 | Hybrid | 3.0 | 1.5 | 25% |
| 2 | 0.29 | Hybrid | 3.0 | 1.8 | 37% |
| 3 | 0.43 | Hybrid | 3.0 | 2.1 | 49% |
| 4 | 0.57 | Hybrid | 3.0 | 2.3 | 61% |
| 5 | 0.71 | Hybrid | 3.0 | 2.6 | 74% |
| 6 | 0.86 | Hybrid | 3.0 | 2.8 | 86% |
| 7 | 1.00 | Continuous | 3.0 | 3.0 | 100% |

As shown in FIG. 5, retinal image quality is optimized for Fresnel and hybrid Fresnel-continuous phase correctors of between approximately 2 and 4 diopters due to the compensatory dispersive properties of diffractive discontinuities in the wavefront aberration.

Retinal image quality in FIG. 5 was quantified by computing the polychromatic Strehl ratio. The Strehl ratio is defined as the ratio of the maximum value of the test-case polychromatic point spread function ($PSF_{poly}$) divided by the aberration-free (i.e. diffraction-limited) $PSF_{poly}$. $PSF_{poly}$ is defined below, as the weighted sum of monochromatic point spread functions (PSF) with relative defocus ($W(\lambda)$, shown below) defined by the longitudinal chromatic aberration of the eye ($C_2^0$).

$$PSF_{poly}(x, y) = \frac{1}{a} \sum_{\lambda=405\ nm}^{695\ nm} V_\lambda(\lambda) PSF\left(x, y, e^{-i\frac{2\pi}{\lambda}[W(\lambda)]}\right)$$

$$W(\lambda) = C_\lambda^0(\lambda) \cdot \sqrt{3}\,(2\rho^2 - 1)$$

Figure 6A:
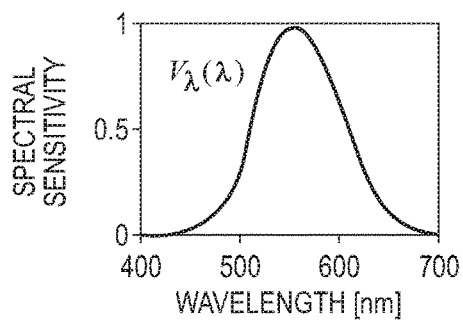
FIGS. 6a and 6b are graphs of the weighting-coefficient $V_\lambda$ specified by the human eye's spectral sensitivity used in calculation of the polychromatic Strehl ratio, and of the longitudinal chromatic aberration of the eye ($C_2^0$) used in calculating the relative defocus $W(\lambda)$, also used in calculating the polychromatic Strehl ratio.
Figure 6B:
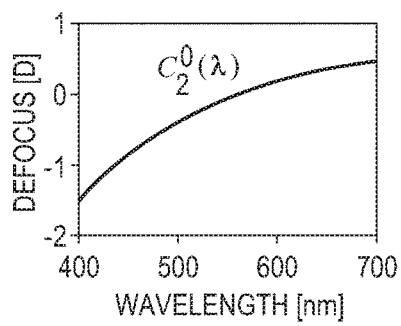

The weighting-coefficients, $V_\lambda$, of the sum are specified by the human eye's spectral sensitivity, shown in FIG. 6a. The longitudinal chromatic aberration of the eye is plotted in FIG. 6b.

To estimate expected visual acuity with the lens designs, we used a retinal image quality metric (Image Convolution Metric) which is very well correlated with high-contrast visual acuity ($R^2$=0.82). The image convolution metric is described in detail elsewhere ("Modified monovision with spherical aberration to improve presbyopic through-focus visual performance." Zheleznyak, Len, Ramkumar Sabesan, Je-Sun Oh, Scott MacRae, and Geunyoung Yoon. Investigative ophthalmology & visual science 54, no. 5 (2013): 3157-3165; "Impact of pupil transmission apodization on presbyopic through-focus visual performance with spherical aberration." Zheleznyak, Len, HaeWon Jung, and Geunyoung Yoon. Investigative ophthalmology & visual science 55, no. 1 (2014): 70-77). In brief, it convolves an image (such as a resolution target) with the polychromatic point spread function described above. The correlation between the convolved image with an unaberrated reference image is calculated. This value was then correlated with visual acuity data measured in subjects using an adaptive optics vision simulator.

Example: Pupil-Independent Hybrid Lens Designs

In addition to mixed, or hybrid, Fresnel and continuous phase profiles which are allocated per inner/outer regions of the optical zone (i.e. pupil), hybridization may be implemented throughout the pupil. This is achieved by increasing the phase-wrap wavefront height to multiples of the design wavelength (i.e. λ, 2λ, 3λ, etc.). By increasing the Fresnel-lens step height, the number of discontinuities in the wavefront is decreased, as shown in FIGS. 7b and 7c relative to FIG. 7a. Similar to the pupil-dependent designs, phase-correctors with larger numbers of discrete wavefront steps contribute to the cancellation of the eye's native longitudinal chromatic aberration. Further embodiments of the invention may employ a lens wherein different degrees of hybridization are implemented in the central continuous zone and the outer discontinuous region having phase heights in even-integer multiples of π (e.g. 2π, 4π, 6π and so on).

Figure 7A:
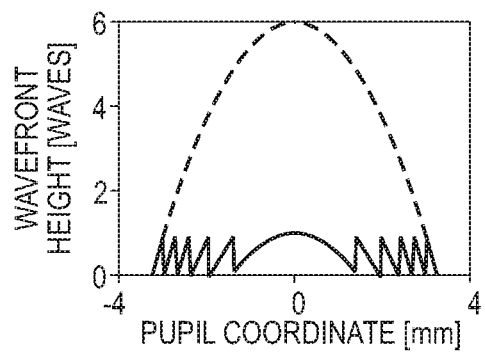
FIGS. 7a, 7b and 7c schematically illustrate wavefront cross-sections of parabolic phase shift refractive correctors having various phase-wrap wavefront heights and number of discrete wavefront steps.
Figure 7B:
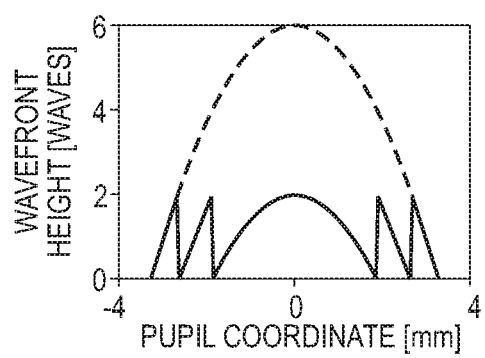
Figure 7C:
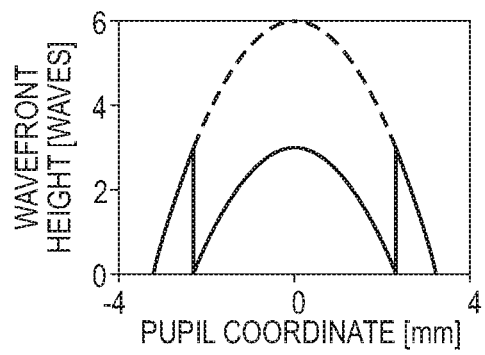
Figure 8:
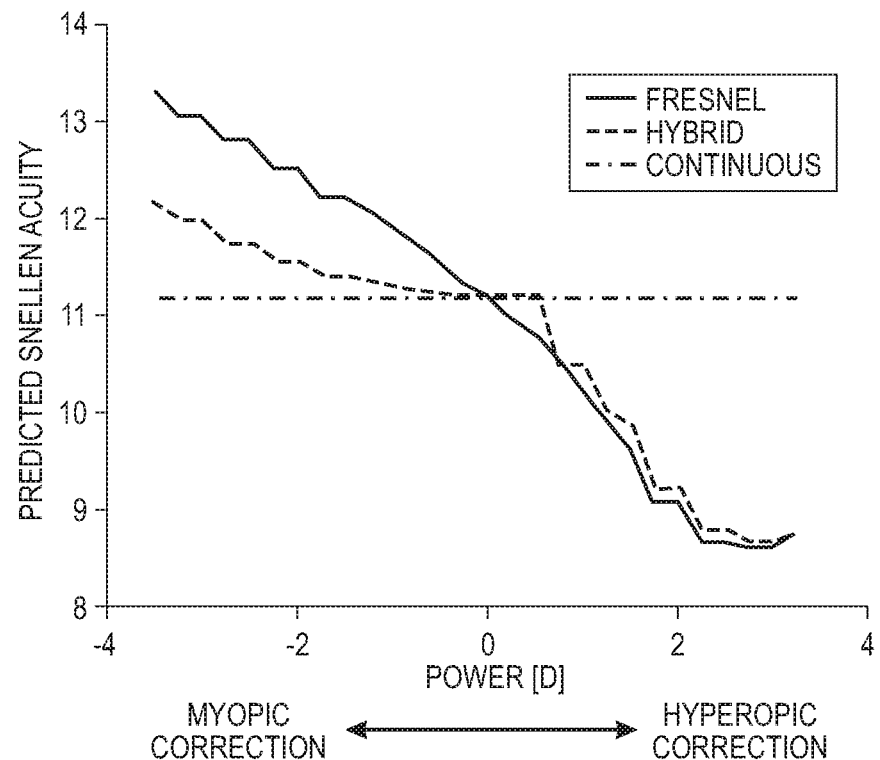
FIG. 8 is a graph depicting predicted visual acuity for a range of dioptric powers for Fresnel, hybrid and continuous lens designs.

FIG. 8 depicts predicted visual acuity for a range of dioptric powers for simple continuous parabolic phase shifts and corresponding complete modulo phase wrapped Fresnel lens designs and hybrid continuous/Fresnel lens designs of the type illustrated in FIGS. 7a-7c, where the Hybrid line refers to results for designs with 10π (i.e., 5 waves of phase height) for each refractive zone. The simulation was done with a 6.5 mm pupil diameter in an aberration-free model eye.

As shown in FIG. 8, continuous (dot-dash line) lenses maintain a constant visual acuity for both positive and negative dioptric powers. Alternatively, conventional modulo 2π phase wrapped Fresnel lenses (solid line) interact with polychromatic optical quality (and thus visual performance) due to their dispersive property of a negative Abbe number (−3.45). Therefore, Fresnel lenses improve visual acuity for positive powers, whereas negative powers degrade visual acuity. Finally, hybrid lenses (dash line) fall between the continuous and Fresnel lens designs, maintaining most of the improvement seen for Fresnel lenses for positive powers, and providing improved visual acuity relative to the Fresnel lenses for negative powers.

Example: Other Lens Designs

Figure 9:
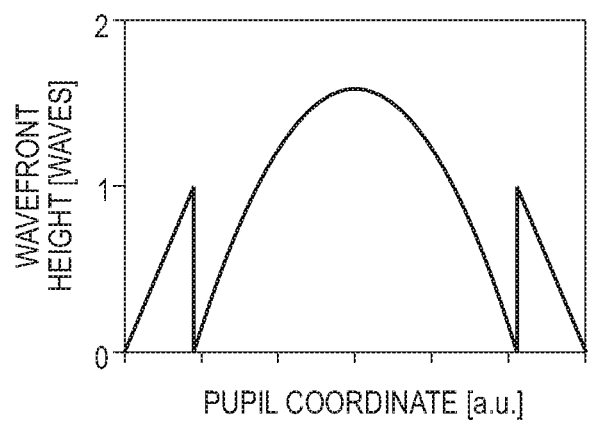
FIG. 9 schematically illustrates a wavefront cross-section of a refractive corrector in accordance with an embodiment.

In addition to simple parabolic phase shifters, the described concept of mixed continuous central zone with discontinuous peripheral areas can be employed for other phase profiles, such as, e.g., hyperbolic phase profiles, aspheric phase profiles, and free-form/arbitrary phase profiles. Hyperbolic phase profiles may be employed, e.g., for adding multifocality, as well as other known uses. Aspheric phase profiles with spherical aberrations (4th order and higher), may be employed to extend the depth of focus ("Subjective depth of field in presence of 4th-order and 6th-order Zernike spherical aberration using adaptive optics technology," Benard, Yohann, Norberto Lopez-Gil, and Richard Legras, Journal of Cataract & Refractive Surgery 36.12 (2010): 2129-2138). FIG. 9 depicts a cross-section of a hybrid wavefront with defocus and spherical aberration. Free-form/arbitrary phase profiles may be employed, e.g., to correct the native higher order aberration profiles of individuals.

It will be appreciated that variants of the above-disclosed embodiments and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A refractive corrector comprising:
   (a) a central zone having a continuous wavefront cross-section phase profile, having a wavefront maximum height of greater than 1 design wavelength λ in the area of the central zone; and
   (b) a peripheral region comprising multiple segments and having a discontinuous wavefront cross-section phase profile having phase shifts between segments that are equal to the design wavelength or multiples of the design wavelength, and wherein the phase shifts in the peripheral region are less than the wavefront maximum height in the central zone;
   wherein the refractive corrector comprises an optical, polymeric lens material having an anterior surface and posterior surface and an optical axis intersecting the surfaces, and at least one laser-modified layer disposed between the anterior surface and the posterior surface formed by scanning light pulses from a laser along regions of the optical, polymeric material to cause changes in the refractive index of the polymeric lens material, and wherein the at least one laser-modified layer forms at least part of each of the central zone and the peripheral region formed by varying the refractive index of the materials forming each of the central zone and peripheral region across each of the central zone and peripheral region.

2. The refractive corrector of claim 1, wherein the peripheral region has a Fresnel structure having a phase shift between segments equal to the design wavelength.

3. The refractive corrector of claim 1, wherein the peripheral region circumscribes the central zone.

4. The refractive corrector of claim 1, wherein an outer perimeter of the central zone and an outer perimeter of the peripheral region are circular.

5. The refractive corrector of claim 1, wherein an optical surface of the central zone is parabolic.

6. The refractive corrector of claim 1, wherein an optical surface of the central zone is hyperbolic.

7. The refractive corrector of claim 1, wherein an optical surface of the central zone is a freeform surface.

8. The refractive corrector of claim 1, wherein an optical surface of the central zone is aspheric.

9. The refractive corrector of claim 1, wherein a diameter of the central zone is from 20% to 90% of the outer diameter of the peripheral region.

10. The refractive corrector of claim 1, wherein the central zone and the peripheral region are located in a contact lens.

11. The refractive corrector of claim 1, wherein the central zone and the peripheral region are located in an intra-ocular lens.

12. The refractive corrector of claim 1, wherein the phase shifts between segments in the discontinuous wavefront cross-section phase profile in the peripheral region are $2\pi$ phase shift discontinuities.

13. The refractive corrector of claim 1, wherein the at least one laser-modified layer includes a first portion having a continuous variation in index of refraction forming the central zone, and additional portions having discontinuous variations in index of refraction forming the peripheral region.

14. The refractive corrector of claim 1, wherein the refractive corrector is mono-focal for the design wavelength.

15. The refractive corrector of claim 1, wherein the design wavelength is a wavelength between 400 and 700 nm.

16. The refractive corrector of claim 1, wherein the design wavelength is 555 nm.

17. A method of forming a refractive corrector comprising:
    providing an optical, polymeric lens material having an anterior surface and posterior surface and an optical axis intersecting the surfaces; and
    forming at least one laser-modified layer disposed between the anterior surface and the posterior surface with light pulses from a laser by scanning the light pulses along regions of the optical, polymeric material to cause changes in the refractive index of the polymeric lens material;
    wherein the optical, polymeric lens material comprises (a) a central zone having a continuous wavefront cross-section phase profile, having a wavefront maximum height of greater than 1 design wavelength λ in the area of the central zone, and (b) a peripheral region comprising multiple segments and having a discontinuous wavefront cross-section phase profile having phase shifts between segments that are equal to the design wavelength or multiples of the design wavelength, wherein the phase shifts in the peripheral region are less than the wavefront maximum height in the central zone;
    and wherein the at least one laser-modified layer forms at least part of each of the central zone and the peripheral region by varying the refractive index of the materials forming each of such central zone and peripheral region across each of such central zone and peripheral region.

18. The method of claim 17, wherein the at least one laser-modified layer includes a first portion having a continuous variation in index of refraction forming the central zone.

19. The method of claim 18, wherein the at least one laser-modified layer includes additional portions having discontinuous variations in index of refraction forming the peripheral region.

20. A method for modifying a refractive property of ocular tissue in an eye, comprising:
    forming at least one optically-modified layer in at least one of the corneal stroma and the crystalline lens ocular tissue in an eye by scanning light pulses from a laser focused in the corneal stroma or crystalline lens ocular tissue along regions of the corneal stroma or crystalline lens ocular tissue to cause changes in the refractive index within the ocular tissue to form a modified corneal stroma or crystalline lens;
    wherein the modified corneal stroma or crystalline lens comprises (a) a central zone having a continuous wavefront cross-section phase profile, having a wavefront maximum height of greater than 1 design wavelength λ in the area of the central zone, and (b) a peripheral region comprising multiple segments and having a discontinuous wavefront cross-section phase profile having phase shifts between segments that are equal to the design wavelength or multiples of the design wavelength, wherein the phase shifts in the peripheral region are less than the wavefront maximum height in the central zone;
    and wherein the at least one optically-modified layer forms at least part of each of the central zone and the peripheral region by varying the refractive index of the ocular tissue forming each of such central zone and peripheral region across each of such central zone and peripheral region.

21. The method of claim 20, wherein the at least one optically-modified layer includes a first portion having a continuous variation in index of refraction forming the central zone.

22. The method of claim 21, wherein the at least one optically-modified layer includes additional portions having discontinuous variations in index of refraction forming the peripheral region.

23. The method of claim 20, wherein the at least one optically-modified layer is formed in the corneal stroma.

* * * * *